United States Patent
Keum et al.

(10) Patent No.: US 7,255,883 B2
(45) Date of Patent: Aug. 14, 2007

(54) AGENT FOR REDUCTION OF SCAR FORMATION BY USING WOUND ALKALINIZATION

(75) Inventors: Ki Chang Keum, Seoul (KR); Naechoon Yoo, Seoul (KR); Won-min Yoo, Seoul (KR)

(73) Assignee: Healagenics, Inc., Woburn, MA (US)

( * ) Notice: Subject to any disclaimer, the term of this patent is extended or adjusted under 35 U.S.C. 154(b) by 286 days.

(21) Appl. No.: 10/312,097

(22) PCT Filed: Jun. 20, 2001

(86) PCT No.: PCT/IB01/01803

§ 371 (c)(1),
(2), (4) Date: Mar. 17, 2003

(87) PCT Pub. No.: WO02/30432

PCT Pub. Date: Apr. 18, 2002

(65) Prior Publication Data

US 2003/0180390 A1    Sep. 25, 2003

(30) Foreign Application Priority Data

Jun. 23, 2000  (KR) ............................... 2000/34740

(51) Int. Cl.
  *A01N 59/00*  (2006.01)
  *A61K 33/00*  (2006.01)

(52) U.S. Cl. .................................................... 424/717
(58) Field of Classification Search .................... 424/1
  See application file for complete search history.

(56) References Cited

U.S. PATENT DOCUMENTS

| 4,659,572 A | * | 4/1987 | Murray ........................ 424/448 |
| 5,209,724 A | * | 5/1993 | Dhaliwal et al. ........... 424/686 |
| 5,520,926 A |   | 5/1996 | Ferguson |

(Continued)

FOREIGN PATENT DOCUMENTS

CN    1156042    8/1997

(Continued)

OTHER PUBLICATIONS

Jullien et al., "Acidic Cellular Environments: Activation of Latent TGF-Beta and Sensitization of Cellular Responses to TGF-Beta and EGF," Int. J. of Cancer 43(5):886-891, May 1989.

(Continued)

*Primary Examiner*—Carlos Azpuru
*Assistant Examiner*—Casey Hagopian
(74) *Attorney, Agent, or Firm*—King & Spalding LLP (57) ABSTRACT

The present invention relates to an agent for reducing scar formation, which inhibits the scar formation by injecting sodium bicarbonate to the dermis tissue of the wound with a syringe to directly control pH of the wound site, namely, by alkalinizing the wound to inactivate TGF-$\beta$. According to the present invention, the agent for reducing scar formation by controlling the wound healing process can be clinically and immediately applied to the treatment of tylosis scar and keloid, etc., and is effective to the treatment of intractable fibrosis diseases. Also, the invention can be widely applied in many ways as an easy tool which can control the action of TGF-$\beta$ in a living organism.

6 Claims, 7 Drawing Sheets

U.S. PATENT DOCUMENTS

| | | | |
|---|---|---|---|
| 5,731,298 | A | 3/1998 | Reinmuller |
| 6,048,844 | A | 4/2000 | Falk et al. |
| 6,063,406 | A * | 5/2000 | Hornack .................... 424/678 |
| 2002/0031555 | A1 | 3/2002 | Siamon |
| 2004/0019011 | A1 | 1/2004 | Falk et al. |
| 2005/0136126 | A1 | 6/2005 | Keum et al. |
| 2005/0142208 | A1 | 6/2005 | Yoo et al. |

FOREIGN PATENT DOCUMENTS

| | | |
|---|---|---|
| CN | 1270812 | 10/2000 |
| EP | 497724 A1 | 8/1992 |
| FR | 2770779 A1 | 5/1999 |
| WO | WO 93/08811 A1 | 5/1993 |
| WO | WO 03/094937 A1 | 11/2003 |

OTHER PUBLICATIONS

Baroni et al., "Sodium Bicarbonate Treatment Reduces Renal Injury, Renal Production of Transforming Growth Factor-Beta, and Urinary Transforming Growth Factor-Beta Excretion in Rats with Doxorubicin-Induced Nephropathy," Am. J. of Kidney Diseases 34(2):328-337, Aug. 1999.

Fuchs et al., "Dirt Tattooing following an explosion in a Chemistry class," Occupational and Environmental Dermatoses 32(4):138-140, 1984.

Border, W.A., et al., "Transforming growth factor-beta in disease: the dark side of tissue repair," *J. Clin. Investig.*, 90(1):1-7 (1992).

ANONYMOUS, "Arm & Hammer Peroxicare Baking Soda Toothpaste," Household Products Database from National Institutes of Health National Library of Medicine, pp. 1-2 (Mar. 2000). Online. Internet. Accessed on Nov. 8, 2006. http://hpd.nlm.nih.gov/cgibin/household/brands?tbl=brands&id=3005032.

Arm & Hammer, "Arm & Hammer Dental Care toothpaste was introduced nationally in 1988," *Arm & Hammer Milestones 150th Anniversary*, pp. 8 of 9 (1996). Online. Internet. Accessed on Nov. 8, 2006. <http://www.churchdwight.com/contact/downloads/cd150.pdf>.

Brown, P.D., et al., "Physicochemical activation of recombinant latent transforming growth factor-beta's 1, 2, and 3," *Growth Factors*, 3(1):35-43 (1990).

Arm & Hammer Peroxicare Baking Soda Toothpaste (Internet Accessed on Oct. 24, 2006) (<http://hpd.nlm.nih.gov/cgi-bin/household/brands?tbl=brands&id=305032>, *Household Products Database-National Insitutes of Health/National Library of Medicine*, Mar. 1, 2000.

Arm & Hammer Dental Care toothpaste was introduced nationally in 1988 (Internet Accessed Oct. 24, 2006)(<http://www.churchwight.com/company/comp-milestones.asp>, *Arm & Hammer Marketing Milestones 150th Anniversary*, pp. 8 of 9, Jan. 1, 1996.

* cited by examiner

FIG. 1a scar visible by eye

Narrow

AGENT FOR REDUCTION OF SCAR FORMATION BY USING WOUND ALKALINIZATION

TECHNICAL FIELD

The present invention relates to an agent for reducing scar formation by using alkalinization of the wound, which is clinically easy to apply. More particularly, the present invention relates to an agent for reducing scar formation, which inhibits the scar formation by injecting sodium bicarbonate to the dermis tissue of the wound with a syringe to directly control pH of the wound site, namely, by alkalinizing the wound to inactivate TGF-β.

BACKGROUND ART

There have been efforts to reduce the formation of scar. However, an effective method has not yet been found. It was reported that the wound of a fetus is cured without scar. After such report, trials have been made to reveal the differences between the wound healing process in a fetus and that in a mature individual, change the wound healing process in a mature individual to that in a fetus, and thereby reduce the scar formation. One of the revealed differences is that Transforming Growth Factor-Beta (TGF-β) is not immunochemically detected in the wound of a fetus, but functions in the wound healing process of a mature individual and plays an important role in the scar formation. This fact shows that it would be possible to inhibit the scar formation by controlling TGF-β. Actually, there was a report that the scar formation in a white rat could be reduced by the use of an antibody against TGF-β (*Acidic cellular environments; activation of latent TGF-beta and sensitization of cellular responses to TGF-beta and EGF. International Journal of Cancer,* 43(5):886-91, May 15, 1989). TGF-β is secreted in inactivated state from cells and is mostly present in inactivated state even outside of cells. Only when exposed to a certain specific condition, TGF-β is activated, combines with a receptor of a target cell and functions. Heat, acidic condition, protease, etc. are known as physicochemical conditions which can activate TGF-β (*Physicochemical activation of recombinant latent transforming growth factor-beta's* 1, 2, and 3. *Growth Factors.* 3(1):35-43, 1990). However, no studies have been made yet with respect to the reduction of scar formation by using the inactivation of TGF-β. The present invention aims to control the pH of the wound, which is clinically easy to apply, namely, to alkalinize the wound and lead the inactivation of TGF-β, and to confirm whether the inactivation actually reduces the scar formation.

There have been several trials to reduce scar formation by controlling TGF-β which functions during the entire process of scar formation. However, those trials were related to the use of an antibody and have problems in actual application. TGF-β widely functions in a living organism and is under active study in various fields. The processes of formation, secretion and function of TGF-β have not yet been clearly known. According to the facts discovered to date, TGF-β is secreted from cells in inactivated state and functions with a target organ under specific conditions. Heat, acidic pH, and protease are known as the physicochemical conditions which can activate TGF-β. However, no trials have been made to reduce the scar using TGF-β.

DISCLOSURE OF INVENTION

The present invention was conceived based upon the above sated facts. The inventors of the present invention have completed the present invention by controlling the pH of the wound, which is clinically easy to apply, that is, by alkalinizing the wound and inactivating TGF-β, thereby leading the wound healing process which is similar to that of a fetus and confirming that the scar formation is reduced. Accordingly, the objective of the present invention is to provide an agent for reducing scar formation, which inactivates TGF-β, reduces the scar formation and thus heals the wound without scar.

The present invention is directed to a method for reducing scar formation during the wound healing process. TGF-β is known to play an important role in the scar formation process of the wound. To inactivate TGF-β, the wound should be alkalinized. To easily alkalinize the wound, sodium bicarbonate in the concentration of sodium bicarbonate 1 mEq (1 cc)/distilled water 10 cc is injected to the dermis tissue of the wound to directly control pH of the wound, thereby reducing the scar formation of the wound. The pH range which effectively reduces the scar formation, namely, which does not activate TGF-β and alkalinizes the wound, is 9.0-10.0, preferably, 9.2-9.8. Also, sodium bicarbonate of the present invention reduces fibrosis in the process of tissue regeneration or healing, by controlling pH (alkalinization) of the regeneration or healing spot.

EXAMPLES

The following examples disclose the present invention in more detail.

In the wound healing process of an adult white rat, it was histologically studied whether the alkalinization of the wound reduces the scar formation, and it was indirectly confirmed whether such a reduction is caused by TGF-β inactivation, by observing differences of scar leading action of TGF-β between the alkalinized wound and the control wound.

Materials
Animal: forty white rats of Spraue-Dawley origin, which weigh 300-350 mg
    bovine TGF-β
    0.1 mEq sodium bicarbonate Methods of Experiment A. Experiment of Wound Alkalinization (Twenty White Rats)

On the dorsum of adult white rats, skin near the limbs which are on the same distance from the median line was incised in about 10 mm long. After incision, the control group was simply sutured. In sham control group, 0.1 cc distilled water was injected to the dermis of the incised wound. In test group, 0.1 mEq sodium bicarbonate 0.1 cc (Ph 9.5±0.3) was injected to the dermis of the incised wound.
    a. control×1 site: suture only
    b. experimental×1 sites: 0.1 mEq Sodium bicarbonate 0.1 cc injection and suture B. Experiment of TGF-β Inactivation (Twenty White Rats)

On the dorsum of adult white rats, skin near the limbs which are on the same distance from the median line was incised in about 10 mm long. Before suture, TGF-β 0.05 μg was injected to the dermis of the incised wound in test group I, while both TGF-β 0.05 μg and 0.1 mEq sodium bicarbonate 0.1 cc (Ph 9.5±0.3) were injected to the dermis of the incised wound in test group II.
    a. experimental I×1 site: TGF-β injection and suture
    b. experimental II×1 sites: TGF-β+ sodium bicarbonate injection and suture Analysis of the Results A. Histological Observation On 14$^{th}$ and 56$^{th}$ days from the experiments, tissues of ten adult white rats were taken, fixed in 10% neutral buffer formalin for 24 hours, embedded in paraffin throughout the normal tissue treating process. In the middle of the wound, the tissue was cut into 4 μm thick, perpendicularly to the major axis, and dyed with hematoxyline-eosine and Masson's trichrome to observe the connective tissues (FIGS. 1a to 7b).

Figure 1A:
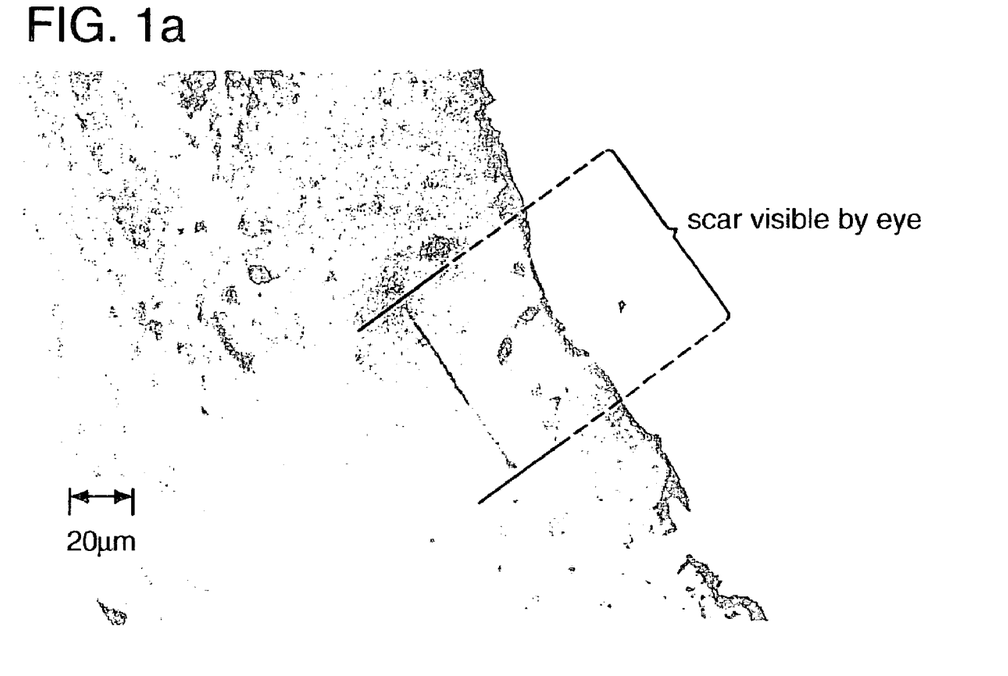
FIG. 1a shows the tissue of the control group after two weeks from the injection of distilled water, instead of sodium bicarbonate(dyeing: hematoxylin-erosin dyeing, magnification: 40×).
Figure 1B:
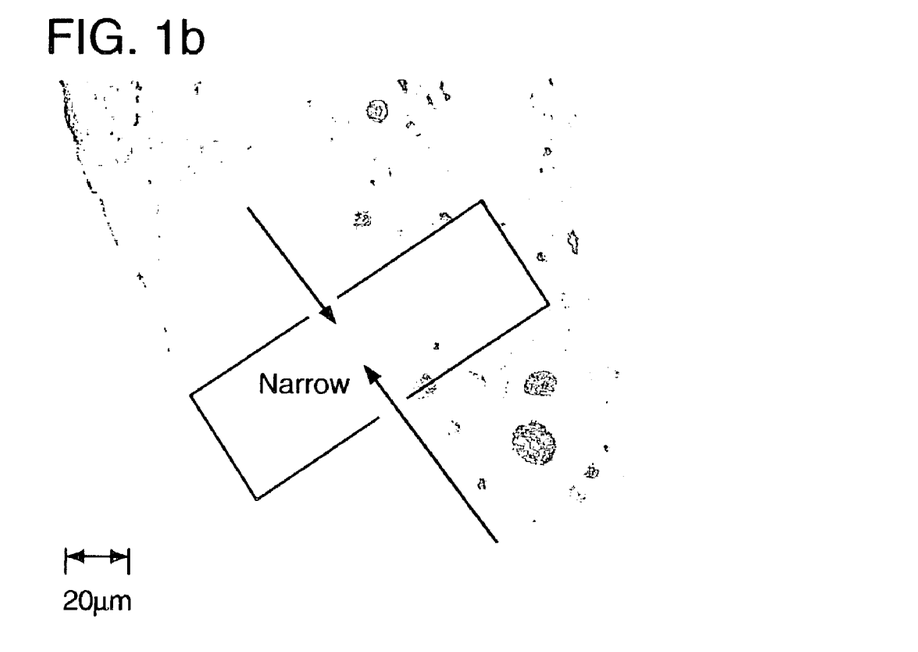
FIG. 1b shows the tissue of the test group after two weeks from the injection of sodium bicarbonate(dyeing: hematoxylin-erosin dyeing, magnification: 40×).

In FIGS. 1a and 1b, control group (a) shows a thicker scar, which is marked with an arrow, than the test group (b).

Figure 2A:
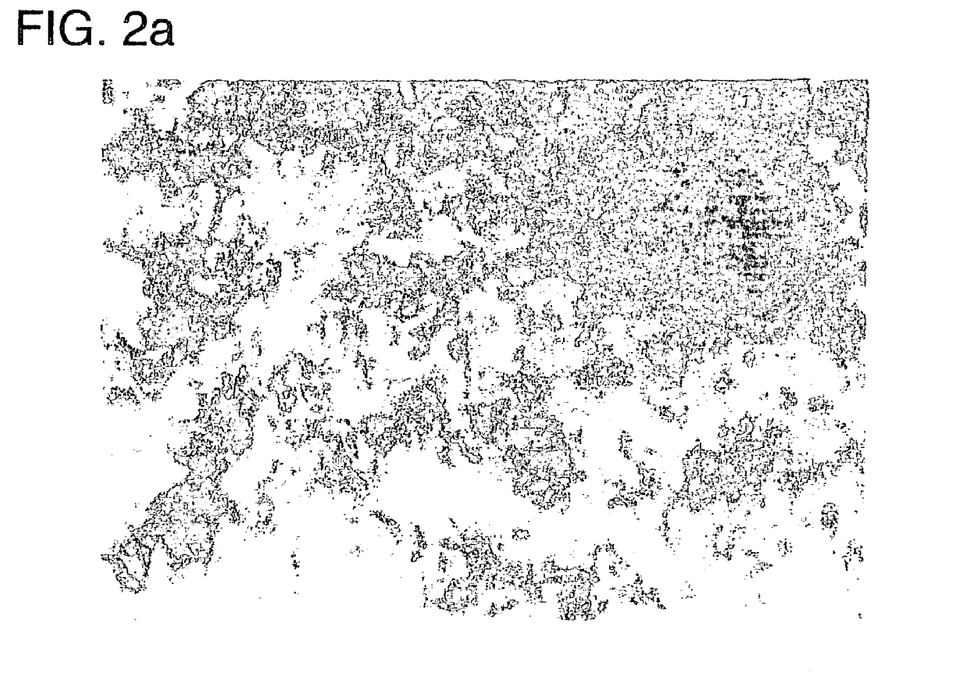
FIG. 2a shows the tissue of the control group after two weeks from the injection of distilled water, instead of sodium bicarbonate(dyeing: trichrome dyeing, magnification: 400×).
Figure 2B:
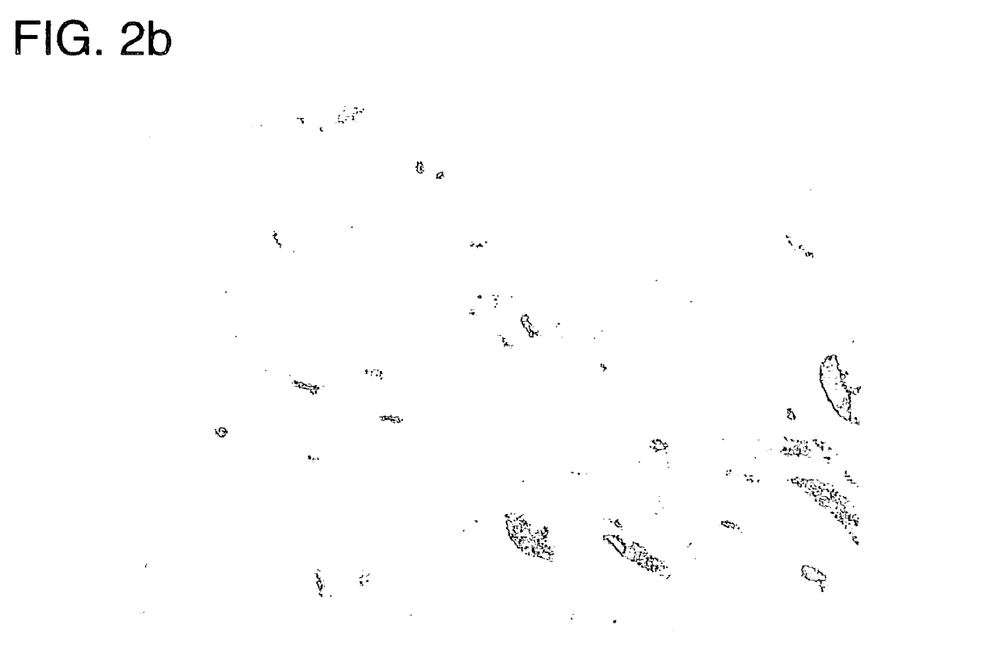
FIG. 2b shows the tissue of the test group after two weeks from the injection of sodium bicarbonate(dyeing: trichrome dyeing, magnification: 400×).

In FIGS. 2a and 2b, control group (a) shows thin, compact, irregular blue-died collagen fibers, which are typical collagen appearance of scar. On the other hand, test group (b) shows relatively thick, regular collagen fibers, which are relatively spacious compared to the control group (a).

Figure 3A:
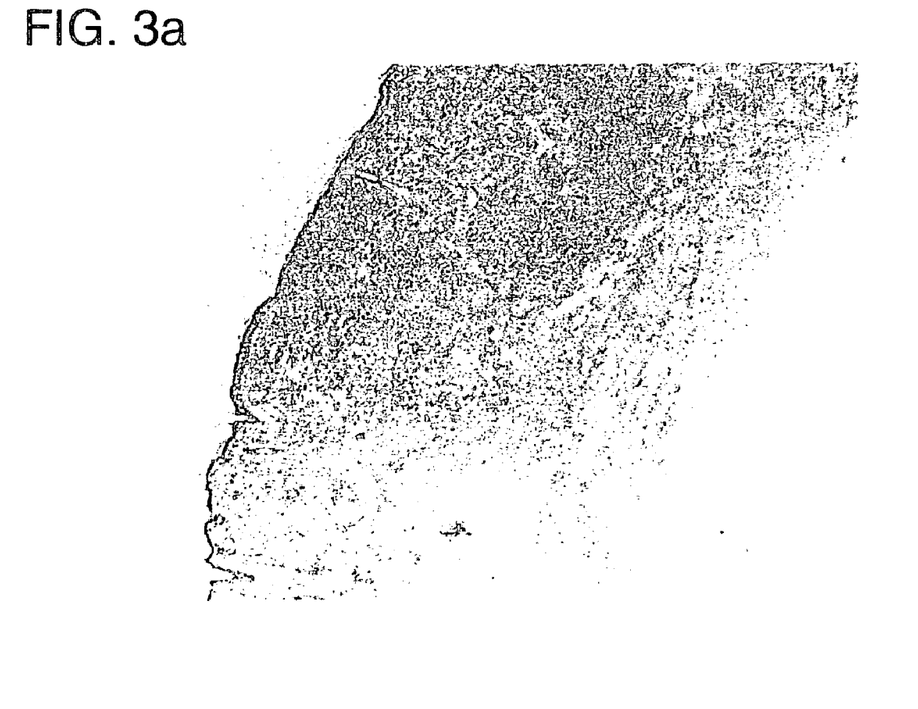
FIG. 3a shows the tissue of the control group after eight weeks from the injection of distilled water, instead of sodium bicarbonate(dyeing: hematoxylin-erosin dyeing, magnification: 40×).
Figure 3B:
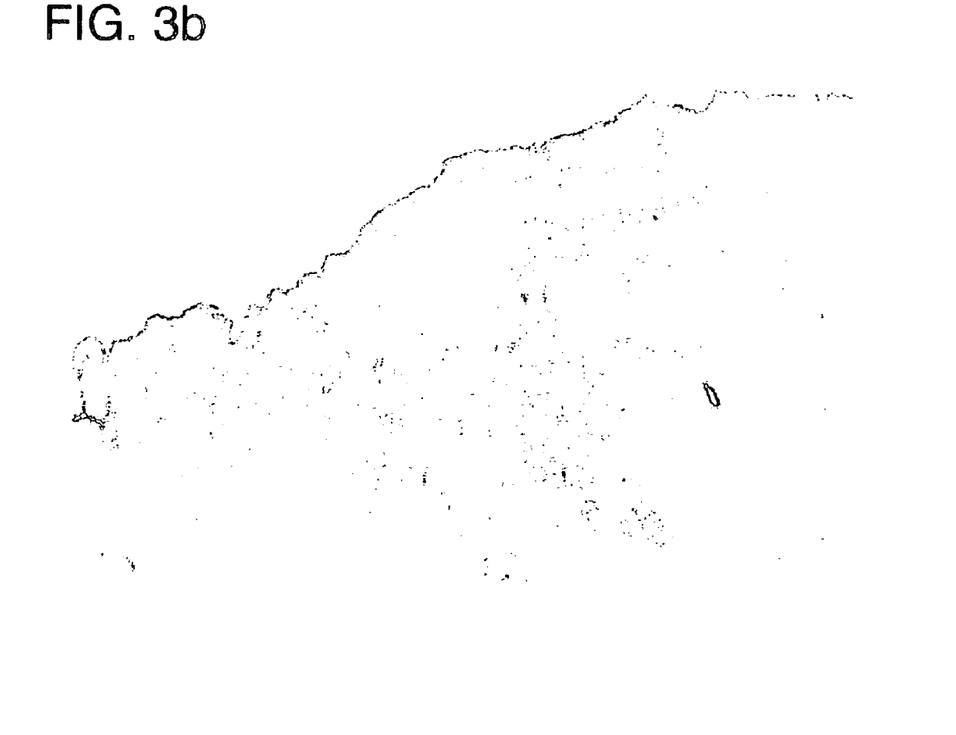
FIG. 3b shows the tissue of the test group after eight weeks from the injection of sodium bicarbonate(dyeing: hematoxylin-erosin dyeing, magnification: 40×).

In FIGS. 3a and 3b, control group (a) shows a thicker scar, which is marked with an arrow, than the test group (b).

Figure 4A:
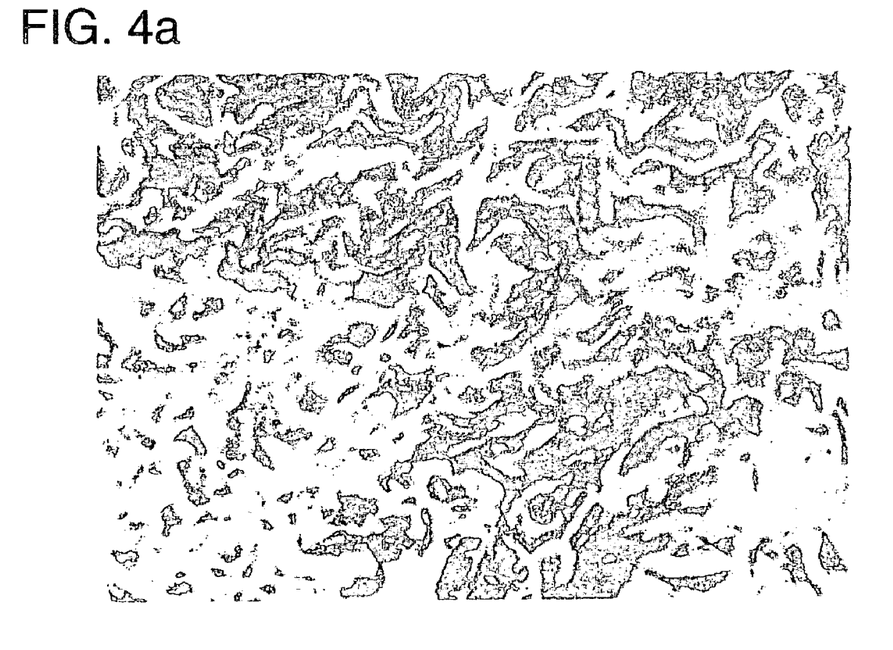
FIG. 4a shows the tissue of the control group after eight weeks from the injection of distilled water, instead of sodium bicarbonate(dyeing: trichrome dyeing, magnification: 400×).
Figure 4B:
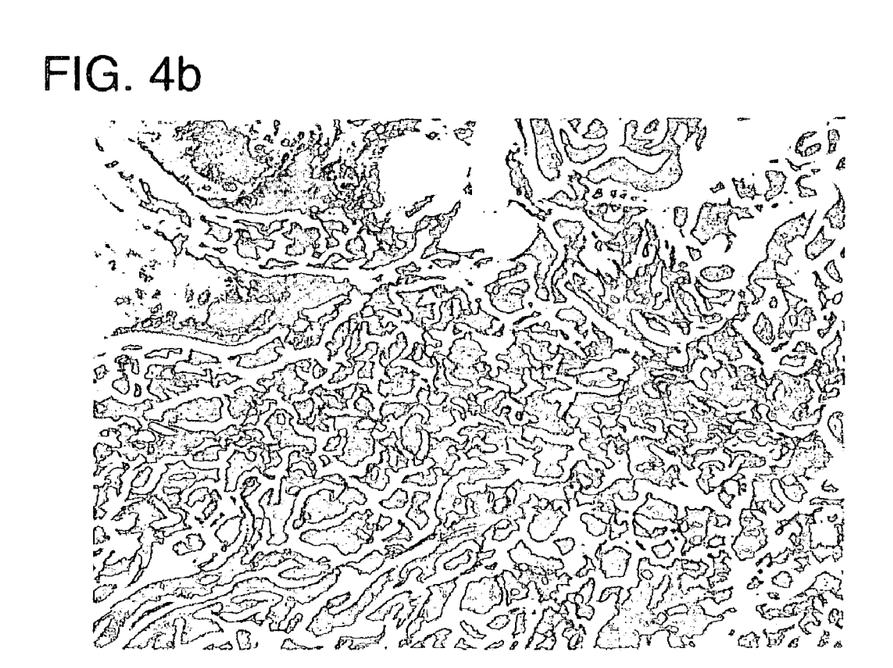
FIG. 4b shows the tissue of the test group after eight weeks from the injection of sodium bicarbonate(dyeing: trichrome dyeing, magnification: 400×).

In FIGS. 4a and 4b, control group (a) shows thin, irregular blue-died collagen fibers, which are typical collagen appearance of scar. On the other hand, test group (b) shows relatively thick, regular collagen fibers, of which structures are almost similar to the normal dermis nearby.

Figure 5A:
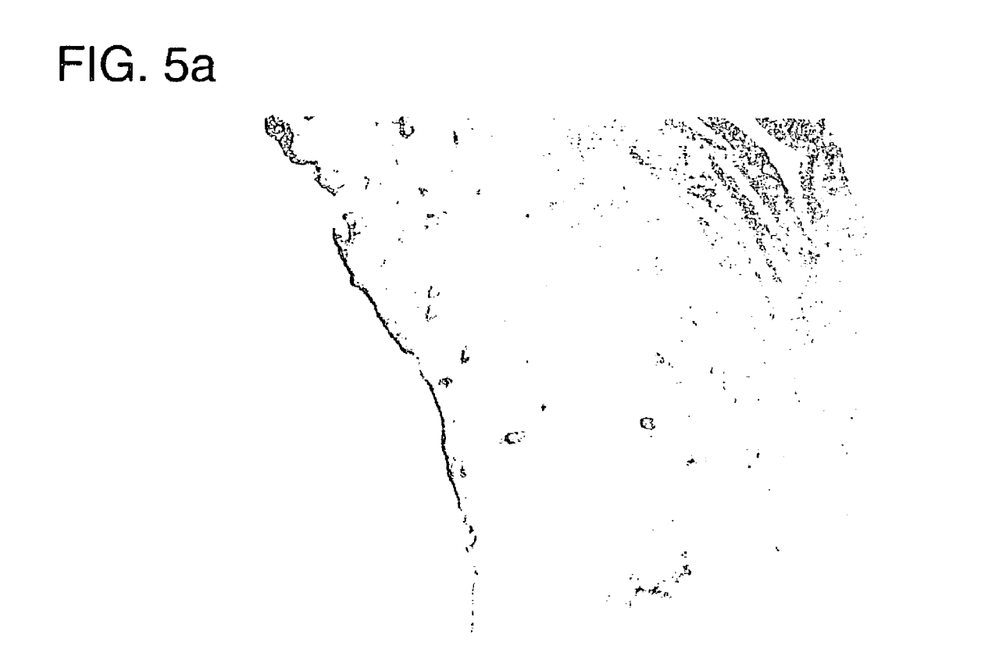
FIG. 5a shows the tissue of the test group after two weeks from the injection of TGF-β (dyeing: hematoxylin-erosin dyeing, magnification: 40×).
Figure 5B:
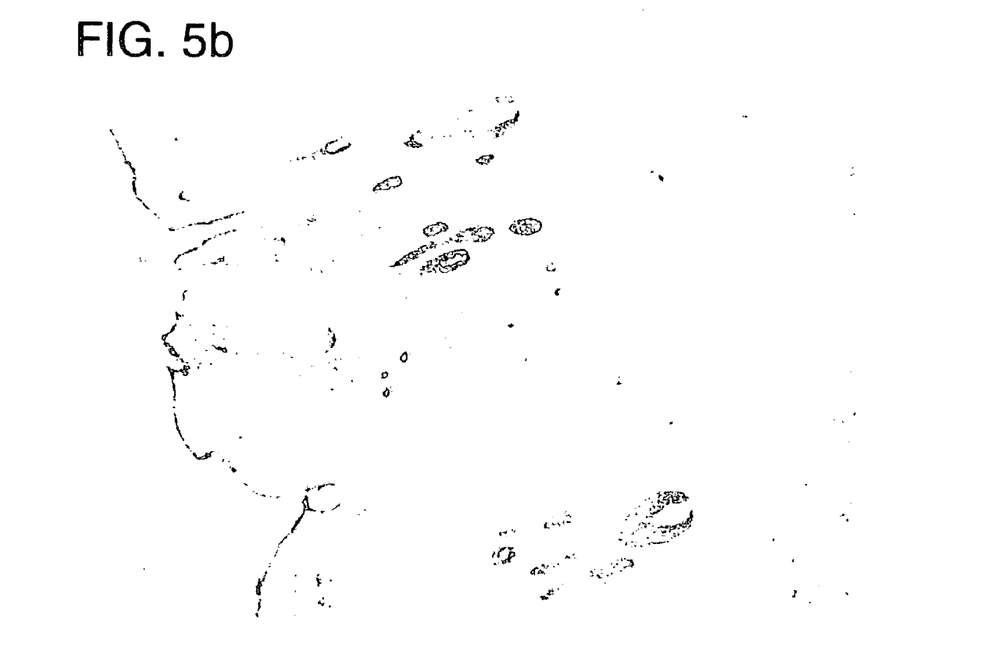
FIG. 5b shows the tissue of the test group after two weeks from the injection of both TGF-β and sodium bicarbonate (dyeing: hematoxylin-erosin dyeing, magnification: 40×).

In FIGS. 5a and 5b, TGF-β injected group (a) shows a thicker scar, which is marked with an arrow, than the test group (b).

Figure 6A:
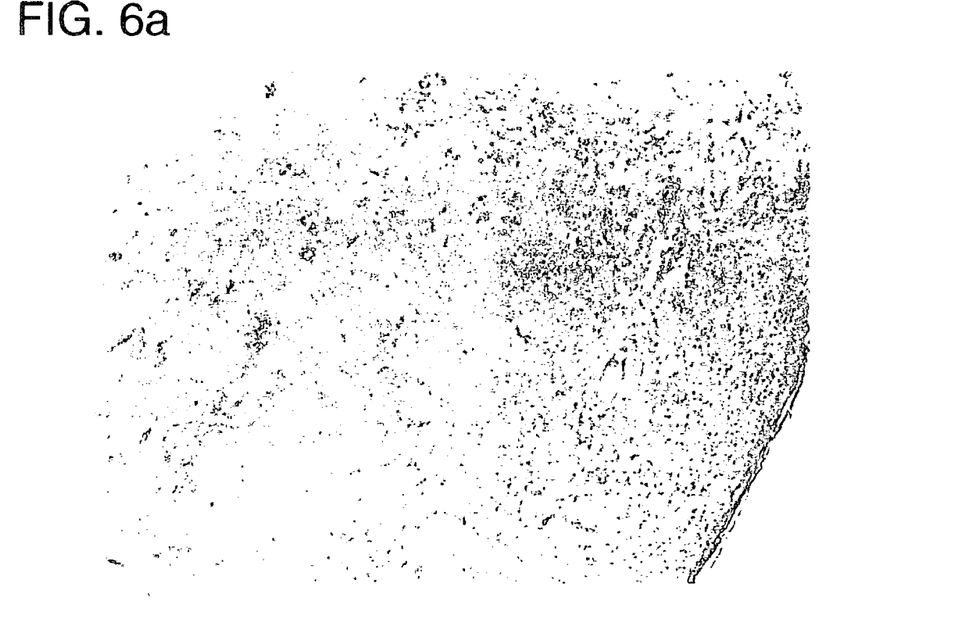
FIG. 6a shows the tissue of the test group after eight weeks from the injection of TGF-β (dyeing: hematoxylin-erosin dyeing, magnification: 100×).
Figure 6B:
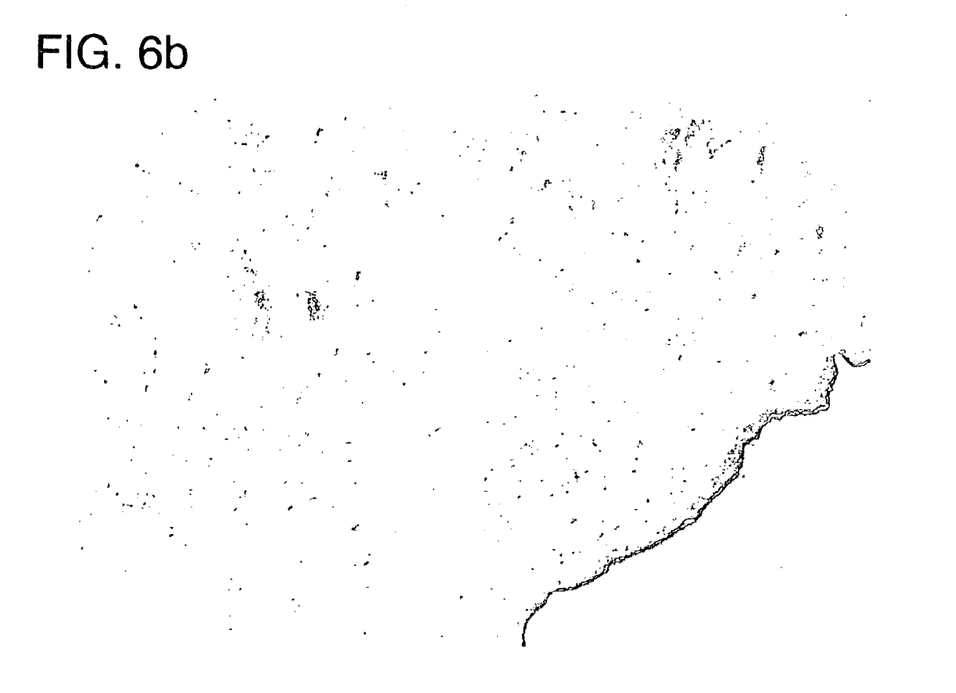
FIG. 6b shows the tissue of the test group after eight weeks from the injection of both TGF-β and sodium bicarbonate(dyeing: hematoxylin-erosin dyeing, magnification: 100×).

In FIGS. 6a and 6b, TGF-β injected group (a) shows a thicker scar, which is marked with an arrow, than TGF-β+ sodium bicarbonate injected group (b). The scar of TGF-β+ sodium bicarbonate injected group (b) is too thin to find, and the structure of the tissue is similar to the normal dermis nearby.

Figure 7A:
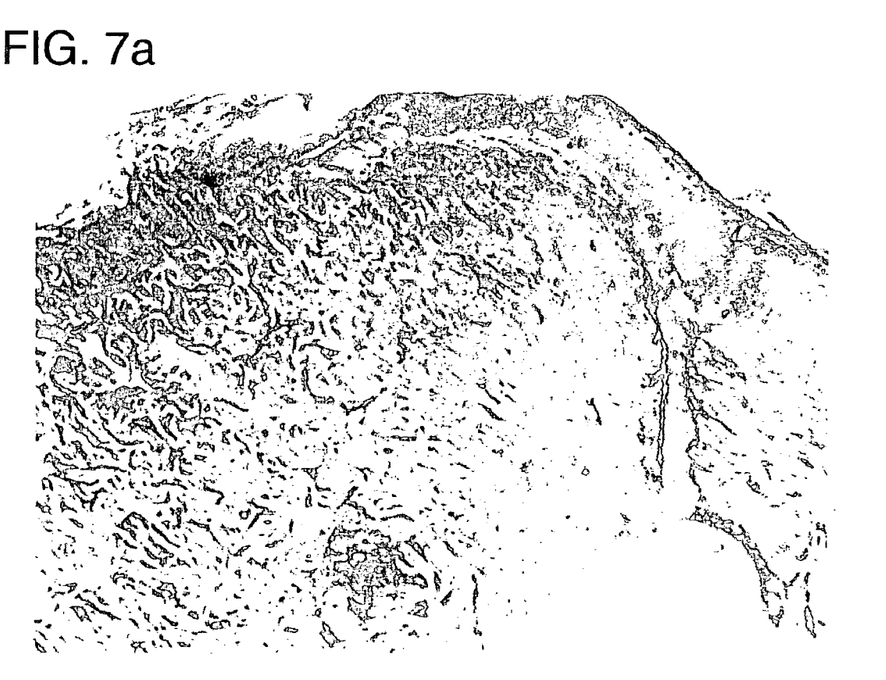
FIG. 7a shows the tissue of the test group after eight weeks from the injection of TGF-β (dyeing: trichrome dyeing, magnification: 400×).
Figure 7B:
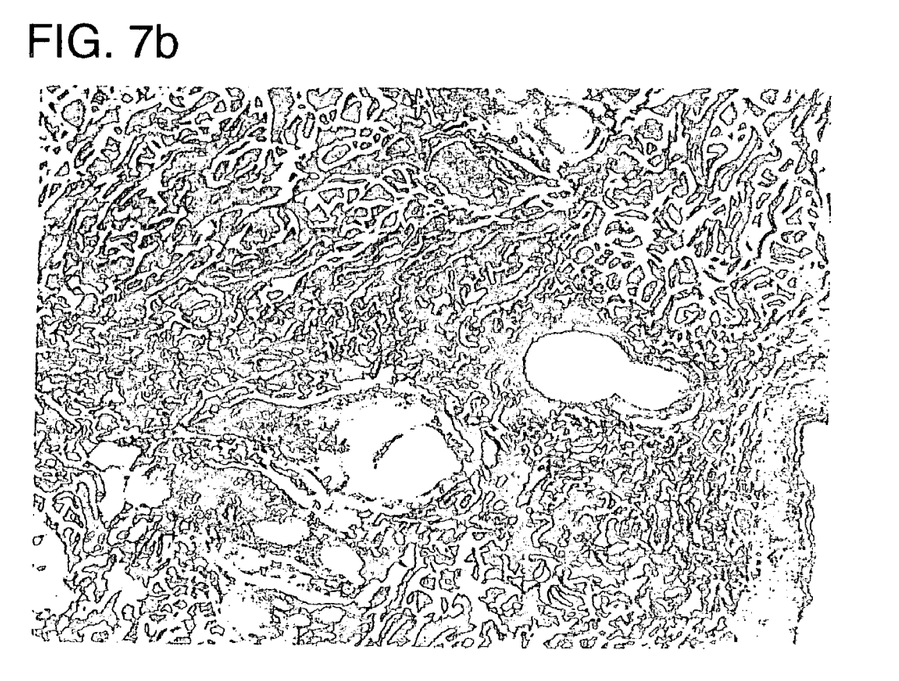
FIG. 7b shows the tissue of the test group after eight weeks from the injection of both TGF-β and sodium bicarbonate(dyeing: trichrome dyeing, magnification: 400×).

In FIGS. 7a and 7b, TGF-β injected group (a) shows thin, irregular blue-died collagen fibers, which are typical collagen appearance of scar, and forms a thick scar. On the other hand, TGF-β+ sodium bicarbonate injected group (b) shows very thin scar and its collagen fibers are thick, regular and of which structure is almost similar to the collagen structure of normal dermis nearby.

B. Measurement of the Width of Scar

With a tissue sample, which was cut perpendicularly to the middle of the wound, the width of the scar by use of image analysis program (Image-Pro version 3.0, Microsoft) under 40 magnification was measured, and the differences between the groups were compared. The result of the measurement was confirmed by Student t-test.

Results

The tissues to be tested were obtained from tested forty white rats, twenty of which were sacrificed at each time, after 2 and 8 weeks from the operational handling.

A. Experiment of Wound Alkalinization

After two (2) weeks from a wound was made, an inflammation was observed from the epidermal tissue layer to the muscular tissue layer at the low magnification (×40) in hematoxylin-eosin dyeing, and there was not much difference between the degree of deposition of inflammatory cells of the test group and the control group. But the width of the scar of test group was thinner than that of the control group (Refer to FIG. 1). The deposited Collagen of Trichrome dyeing was thin and irregular in both the test group and the control group. But the amount of deposition of the Collagen of the test group was meager compared to that of the control group, and deposition of the Collagen of the control group was larger and denser (Refer to FIG. 2).

When the width of scar was measured at magnification of 40, that of the control group was average of 68.44 μm±22.84, and that of the test group was average of 26.66 μm±9.60. As a result of student t-test, the value of p at a significant level of 0.05 of the two groups was the value of 0.01 or less, which was statistically significant difference (Refer to Table 1).

In the hematoxylin-eosin dyeing of the wound after eight (8) weeks from the wound was made, the test group formed a thin and unnoticeable scar and the control group formed a thick and significant scar at the low magnification (×40) (Refer to FIG. 3). At the high magnification (×400), the test group showed thicker and regular Collagen fibers which was not much different from the normal dermis nearby, whereas the control group showed compactly deposited Collagen fiber, which was clearly distinguishable from the normal dermis nearby. Not many of the fibroblast cells were found in the test group but many of them were still found in the control group. In Trichrome dyeing, the density of Collagen fiber in the test group was not different from that of the normal dermis nearby. The fiber was thick and regular, which was recovered closed to the dermis, while since thin and irregular fiber was densely deposited, the control group clearly showed the scar (Refer to FIG. 4). When the width of the scar was measured at 40 magnification, that of the control group was average of 37.67 µm±7.98, and that of the test group was average of 13.89 µm±2.42. As a result of student t-test, the value of p at a significant level of 0.05 of the two groups was the value of 0.01 or less, which was a statistically significant difference (Refer to Table 1).

TABLE 1

Comparison of the width of sodium bicarbonate group and that of control group (measured by using image analysis program, "Image-Pro version 3.0, Microsoft")

| | Control Group* (n = 10) | sodium bicarbonate group* (n = 10) | Value of p |
|---|---|---|---|
| 2 Weeks | 68.44 µm ± 22.84 | 26.66 µm ± 9.60 | 0.01≧ |
| 8 Weeks | 37.67 µm ± 7.98 | 13.89 µm ± 2.42. | 0.01≧ |

*Mean ± SD

B. Experiment of TGF-β Inactivation

After two (2) weeks from a wound was made, an inflammation was observed from epidermal tissue layer to the muscular tissue layer at the low magnification (×40) in hematoxylin-eosin dyeing, and there was not much difference between the degree of deposition of inflammatory cells of TGF-β group and sodium bicarbonate+TGF-β group. But the width of the scar of sodium bicarbonate+TGF-β group was thinner than that of the TGF-β group (Refer to FIG. 5). The deposited Collagen of Trichrome dyeing was thin and irregular in both the test group and the control group. But the amount of deposition of the Collagen of the test group was meager compared to that of the control group, and deposition of the Collagen of the control group was larger and denser.

When the width of scar is measured at magnification of 40, that of the TGF-β group is average of 74.84 µm±15.93, and that of sodium bicarbonate+TGF-β group was average of 35.41 µm±6.90. As a result of student t-test, the value of p at a significant level of 0.05 of the two groups was the value of 0.01 or less, which was a statistically significant difference (Refer to Table 2).

In the hematoxylin-eosin dyeing of the wound after eight (8) weeks from the wound was made, sodium bicarbonate+TGF-β group formed a thinner and less noticeable scar than TGF-β group at the low magnification (×40). The control group formed a thicker and more significant scar than the test group at the low magnification (×40) (Refer to FIG. 6).

At the high magnification (×400) as same as the test of alkalinization of a wound, sodium bicarbonate+TGF-β group showed thicker and regular Collagen fibers which was not much different from the normal dermis nearby.

In Trichrome dyeing, the density of Collagen fiber in sodium bicarbonate+TGF-β group was not that different from the normal dermis tissue nearby. The fiber was thick and regular, which was recovered closed to the dermis tissue, while since thin and irregular fiber was densely deposited, TGF-β group clearly showed the scar (Refer to FIG. 7). When the width of the scar was measured at 40 magnification, that of TGF-β group was average of 72.92 µm±16.04, and that of sodium bicarbonate+TGF-β group was average of 49.09 µm±5.58. As a result of student t-test, the value of p at a significant level of 0.05 of the two groups was the value of 0.01 or less, which was a statistically significant difference (Refer to Table 2).

TABLE 2

Comparison of the width of sodium bicarbonate group and that of the control group (measured by using image analysis program, "Image-Pro version 3.0, Microsoft")

| | TGF-β*(n = 10) | sodium bicarbonate + TGF-β* (n = 10) | Value of p |
|---|---|---|---|
| 2 Weeks | 74.84 µm ± 15.93 | 35.41 µm ± 6.90 | 0.01≧ |
| 8 Weeks | 72.92 µm ± 16.04 | 49.09 µm ± 5.58 | 0.01≧ |

*Mean ± SD

INDUSTRIAL APPLICABILITY

As explained and shown in the Examples above, the agent for reducing scar formation according to the present invention by controlling the wound healing process can be clinically and immediately applied to the treatment of tylosis scar and keloid, etc., and is effective to the treatment of intractable fibrosis diseases. Also, the invention can be widely applied in many ways as an easy tool which can control the action of TGF-β in a living organism.

The invention claimed is:

1. A method for reducing scar formation on a wound, the method comprising:
   injecting into the tissue of the wound a composition consisting of sodium bicarbonate and water, wherein the sodium bicarbonate is in an amount effective to control the pH of the wound in a range from 9.0 to 10.0 and to reduce scar formation.

2. The method of claim 1, wherein the composition is injected into dermis tissue.

3. The method of claim 1, wherein the sodium bicarbonate is in an amount effective to inactivate TGF-β.

4. The method of claim 1, wherein the sodium bicarbonate is in amount effective to control the pH of the wound in a range from 9.2 to 9.8.

5. The method of claim 4, wherein the sodium bicarbonate is present in a concentration in the range of 0.1 mEq sodium bicarbonate (0.1 cc).

6. The method of claim 1, wherein the sodium bicarbonate is present in a concentration of 0.1 mEq sodium bicarbonate (0.1 cc).

* * * * *